United States Patent
Palmerton et al.

(10) Patent No.: US 10,004,856 B2
(45) Date of Patent: Jun. 26, 2018

(54) FILTRATION SYSTEM AND METHOD

(71) Applicant: Buffalo Filter LLC, Lancaster, NY (US)

(72) Inventors: Christopher A. Palmerton, Clarence, NY (US); Samantha Bonano, Williamsville, NY (US); Anthony Lizauckas, III, Williamsville, NY (US); Kyrylo Shvetsov, Tonawanda, NY (US); Daniel R. Palmerton, Elma, NY (US); Gregory J. Pepe, Lancaster, NY (US); Joseph Lynch, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 335 days.

(21) Appl. No.: 14/454,960

(22) Filed: Aug. 8, 2014

(65) Prior Publication Data

US 2015/0112246 A1    Apr. 23, 2015

Related U.S. Application Data

(63) Continuation-in-part of application No. 13/693,035, filed on Dec. 3, 2012, now abandoned.

(60) Provisional application No. 61/565,595, filed on Dec. 1, 2011.

(51) Int. Cl.
 *A61M 13/00* (2006.01)
 *B01D 46/44* (2006.01)

(52) U.S. Cl.
 CPC ..... *A61M 13/003* (2013.01); *A61B 2218/008* (2013.01); *A61M 2202/0225* (2013.01); *A61M 2205/053* (2013.01); *A61M 2205/125* (2013.01); *A61M 2205/3344* (2013.01); *A61M 2205/3368* (2013.01); *A61M 2205/3375* (2013.01); *A61M 2205/3653* (2013.01); *A61M 2205/42* (2013.01); *A61M 2205/502* (2013.01); *A61M 2205/6054* (2013.01); *A61M 2205/75* (2013.01); *A61M 2205/8206* (2013.01); *A61M 2205/8237* (2013.01); *B01D 46/446* (2013.01)

(58) Field of Classification Search
 CPC .............. A61M 13/003; A61M 13/006; A61B 2218/008
 See application file for complete search history.

(56) References Cited

U.S. PATENT DOCUMENTS

| | | | | |
|---|---|---|---|---|
| 4,487,606 | A | * 12/1984 | Leviton | A61M 1/0052 141/59 |
| 4,735,603 | A | * 4/1988 | Goodson | A61B 18/20 600/560 |
| 4,895,144 | A | * 1/1990 | Cook | A61B 18/22 604/30 |

(Continued)

*Primary Examiner* — David Bates
(74) *Attorney, Agent, or Firm* — Timothy W. Menasco, Esq.; Harter Secrest & Emery LLP

(57) ABSTRACT

A laparoscopic filter system having a main unit having an inflow port, an outflow port, a pressure sensing port, a user interface having a power switch, a controller, a pump, and an interface for receiving a detachable filter cartridge, and a detachable filter cartridge configured and arranged to reversibly attach to the interface, the detachable filter cartridge having an inflow pass-through line, an outflow pass-through line, a pressure sensing pass-through line, and a filter media arranged in series with the inflow pass-through line.

20 Claims, 14 Drawing Sheets

(56) References Cited

U.S. PATENT DOCUMENTS

| | | | | |
|---|---|---|---|---|
| 4,906,261 A * | 3/1990 | Mohajer | A61M 1/0054 | 128/205.12 |
| 5,006,109 A * | 4/1991 | Douglas | A61M 13/003 | 600/560 |
| 5,047,010 A * | 9/1991 | Ams | A61M 1/0058 | 600/560 |
| 5,098,375 A * | 3/1992 | Baier | A61M 13/006 | 600/560 |
| 5,181,916 A * | 1/1993 | Reynolds | A61M 1/008 | 604/22 |
| 5,242,474 A * | 9/1993 | Herbst | A61B 18/00 | 417/42 |
| 5,318,516 A * | 6/1994 | Cosmescu | A61B 18/1402 | 604/35 |
| 5,360,396 A * | 11/1994 | Chan | A61M 13/003 | 600/560 |
| 5,476,447 A * | 12/1995 | Noda | A61B 18/1482 | 604/26 |
| 5,578,000 A * | 11/1996 | Greff | A61B 18/00 | 604/22 |
| 5,626,568 A * | 5/1997 | Yeh | A61B 18/00 | 604/315 |
| 5,674,219 A * | 10/1997 | Monson | A61B 18/1402 | 604/22 |
| 5,846,182 A * | 12/1998 | Wolcott | A61B 1/00135 | 128/207.14 |
| 5,968,032 A * | 10/1999 | Sleister | A61B 18/00 | 604/35 |
| 5,997,733 A * | 12/1999 | Wilbur | A61B 18/00 | 210/149 |
| 6,110,259 A * | 8/2000 | Schultz | A61B 18/00 | 55/385.1 |
| 6,203,590 B1 * | 3/2001 | Byrd | B01D 46/0023 | 55/319 |
| 6,336,926 B1 * | 1/2002 | Goble | A61B 17/3423 | 606/34 |
| 6,544,210 B1 * | 4/2003 | Trudel | A61B 18/00 | 604/26 |
| 6,576,033 B1 * | 6/2003 | Booth | B01D 46/002 | 428/36.1 |
| 6,592,543 B1 * | 7/2003 | Wortrich | A61B 18/00 | 55/414 |
| 6,645,197 B2 | 11/2003 | Garrison et al. | | |
| 6,685,665 B2 * | 2/2004 | Booth | A61B 17/3421 | 604/158 |
| 7,285,112 B2 * | 10/2007 | Stubbs | A61B 17/3421 | 128/898 |
| 8,585,646 B2 * | 11/2013 | Lloyd | A61B 18/00 | 604/119 |
| 8,602,983 B2 | 12/2013 | Kleyman | | |
| 8,608,816 B2 * | 12/2013 | Palmerton | A61M 1/0001 | 55/319 |
| 8,641,610 B2 | 2/2014 | Okoniewski et al. | | |
| 8,668,665 B2 | 3/2014 | Gerg et al. | | |
| 2010/0170208 A1 * | 7/2010 | Matula | A61M 13/003 | 55/344 |
| 2011/0028891 A1 | 2/2011 | Okoniewski et al. | | |
| 2013/0281788 A1 | 10/2013 | Garrison | | |
| 2013/0303977 A1 | 11/2013 | Spearman et al. | | |
| 2014/0031631 A1 | 1/2014 | Hall et al. | | |
| 2014/0100517 A1 | 4/2014 | Tran | | |
| 2014/0142495 A1 | 5/2014 | Hertzel et al. | | |

* cited by examiner

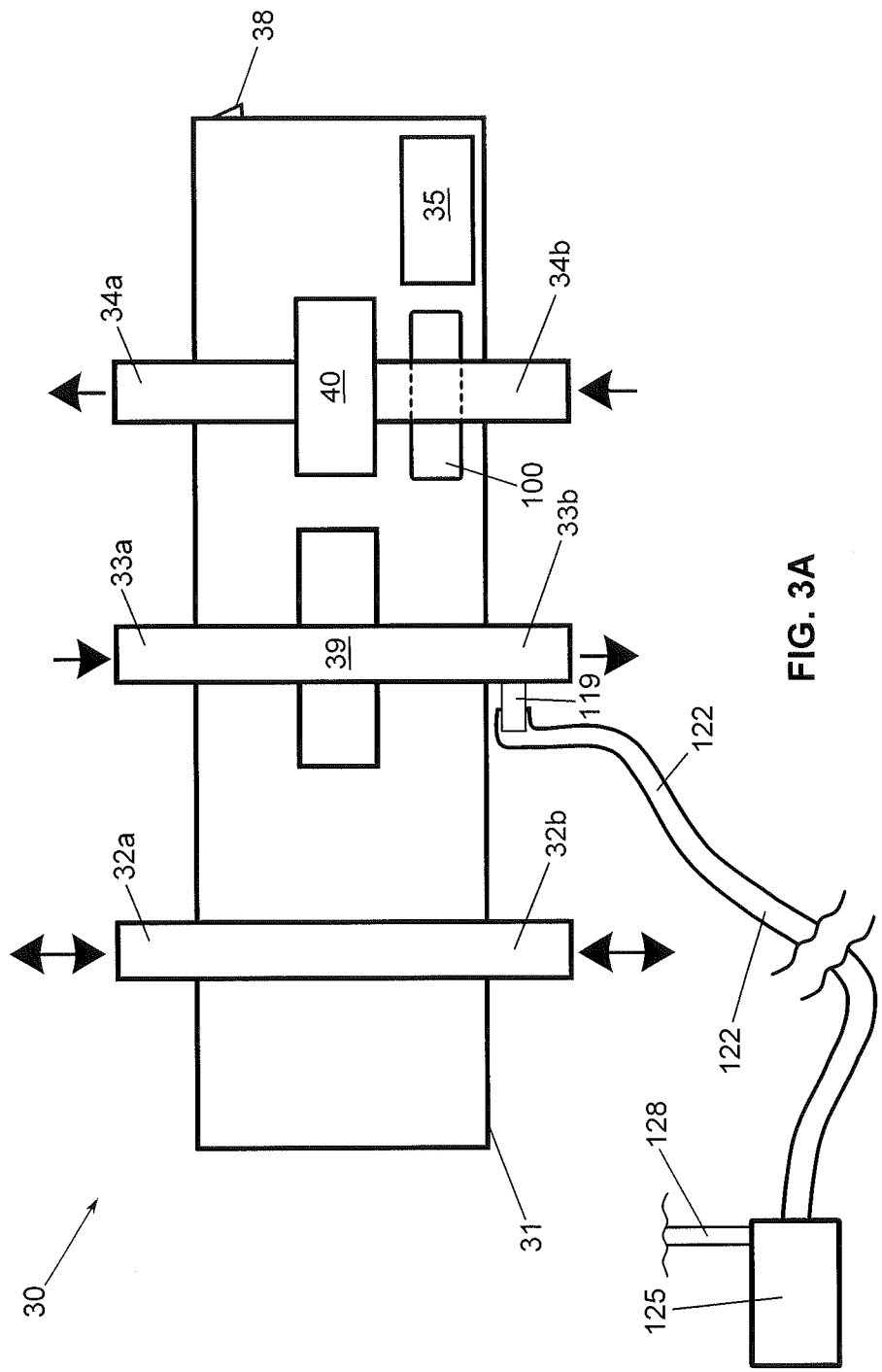

T1 = ignore time period
T2 = measure time period
T3 = measure time period
T4 = sense disconnect time period
T5 = pump shutoff

FILTRATION SYSTEM AND METHOD

CROSS-REFERENCE TO RELATED APPLICATIONS

The present application is a continuation-in-part and claims priority benefit of U.S. patent application Ser. No. 13/693,035 filed on Dec. 3, 2012, which claims benefit of U.S. Provisional Patent Application No. 61/565,595 which was filed on Dec. 1, 2011, both of which are hereby incorporated by reference.

TECHNICAL FIELD

The disclosed system and method relates generally to a filter and, more specifically, to a recirculating gas filter.

BACKGROUND ART

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons. Additional secondary fluids may also be generated from various bodily fluids near the surgery site.

During laparoscopic or minimally invasive surgery, smoke and other particles may become trapped in an insufflated abdomen.

BRIEF SUMMARY OF THE INVENTION

With parenthetical reference to the corresponding parts, portions or surfaces of the disclosed embodiment, merely for purposes of illustration and not by way of limitation, the present embodiments broadly provide a laparoscopic filter system (20) having a main unit housing (19) and a detachable filter cartridge (30). The main unit contains an inflow port (26), an outflow port (25), and may contain a pressure sensing port (27). The ports may contain friction ridges (barbs), Luer-lock style connectors, or other similar interface elements. The main unit also contains a user interface which may have an on/off switch (41), a pressure setting button (42), a clear button (44), an on/off LED (43a), a "pressure in range" LED (43b), a digital or analog pressure reading LED (43c), a filter maintenance LED (43d), or an error LED (43e). The user interface may also contain an LCD, a touch screen, or a touchpad. The main unit also contains a controller (21), which may be a microprocessor, CPU, programmable logic device, or other similar device. The controller may contain memory for storing a pressure setting (71), a high pressure threshold (72), a low pressure threshold (73), and a filter cartridge lifetime state (74).

The main unit also contains the major elements of a pump (23), and pressure sensor (22). A disc filter (47) may also be arranged on the pressure sensor line. The main unit may also have an automatic activation line (46), microphone, or RF sensor, for activating the filter system. An RFID reader and writer may be arranged within the main unit.

The main unit may have a locking notch (28) for retaining the detachable filter and a release button (48) for allowing the detachable filter to be released from the main unit.

The detachable filter cartridge (30) contains a housing (31), an inflow line/tube unit-side port (34a), an inflow line/tube patient-side port (34b), an outflow line/tube unit-side port (33a), and an outflow line/tube patient-side port (33b). The detachable filter cartridge (30) may also contain a pressure sensing line/tube unit-side port (32a) and a pressure sensing line/tube patient-side port (32b).

The detachable filter cartridge (30) contains a first filter (40) arranged on the inflow line and may contain a second filter (39) arranged on the outflow line. The first and second filters may be multilayer, hydrophobic, odor absorbing, or moisture absorbing. The first and second filters may contain ULPA elements or activated charcoal.

The detachable filter cartridge (30) may contain an RFID tag (35), and the RFID tag (35) may contain filter type and state information and may be writeable. The RFID tag (35) may contain data which will be read from the main unit and allow the main unit to properly estimate the detachable filter's lifetime. The detachable filter cartridge (30) may also contain a fluid catch chamber. The housing (31) of the detachable filter cartridge (30) may contain a lock to keep cartridge (30) in main unit (20) and may contain ergonomic friction ridges (50) to allow a user to easily pull the detachable filter (30) out of the main unit (20). The detachable filter cartridge (30) may be formed through ultrasonic welding or snap assembly.

The filter system may be configured to operate following an algorithm (60) which may be specified in software provided in the controller. The algorithm may control the pump through a pump control signal (81) and the user interface through a user interface control signal (82). The pump control signal (81) and user interface control signal (82) may be a function of the on/off state signal (61), the pressure sensor signal (62), the pressure setting button signals (63), the clear button signal (64), current sensor signal (65), or other signals (66). The algorithm may also be a function of the stored pressure setting (71), high pressure threshold (72), low pressure threshold (73), or detachable filter lifetime (74).

The RFID state on the detachable filter cartridge (30) may be written to as a function of filter operating time.

The algorithm may specifically shut off the pump (23) when the pressure reading is greater than the upper threshold, or less than the lower threshold. The algorithm may be configured to shut off the pump (23) only if the thresholds are passed for a time duration. The pressure reading may be low pass filtered.

The filter system (20) may also contain a battery, a signal jack, a remote activation line, or a VGA output signal. The battery may be rechargeable, and the filter system may contain battery recharging circuitry. The filter system may be configured to provide multi-language support. The filter system may contain Bluetooth, Ethernet, wireless Ethernet, RS 232 transceivers or a general RF or audio detectors, and may provide status information or unit activation functionality through these elements.

The filter system (20) may further contain a speaker and the speaker may be used for providing alerts. Some alerts may be for detection of when the filter cartridge (20) is expired, when the pressure is not within a desired range, when remaining battery life has dropped below a threshold, or when a laparoscopic line is disconnected or occluded.

The filter system (20) may further contain a power adapter (49) which provides the ability to be driven by an AC power supply, and may provide support for international AC power specifications. The power interface may also contain an emergency battery for allowing the unit to operate or safely shutdown after a power failure. The filter system (20) may also contain a pressure relief valve to prevent pressure from exceeding a desired threshold. An ultraviolet lamp may be included and configured to disinfect fluid passing through the filter system.

The filter system may also contain an attachment adapter for attaching the filter system to an IV pole, a bedside, a boom, a shelf, and/or a stand. The filter system may further contain acoustical insulation or vibration damping material.

The pump (23) may be a rolling piston pump. The pump (23) may be a high pressure, low volume pump. The pump (23) may be low noise and low vibration and may be configured to push gases through smaller openings without flow degradation.

In one aspect, a new apparatus and system described and illustrated herein is designed to improve and/or maximize smoke evacuation from an abdominal cavity or other area. In another aspect, the new apparatus and system recirculates $CO_2$ or other gases within the abdominal cavity. In another aspect, it keeps abdominal pressure constant and/or minimizes the loss of $CO_2$.

In another aspect, a cleaning filter cartridge (200) is provided to clean the main unit. The cleaning filter cartridge (200) may contain an alcohol or other disinfectant, and the alcohol or disinfectant may pass through the main unit (20) during a cleaning cycle.

In one embodiment, the smoke evacuation apparatus and system can be mounted on the patient bed or attached to nearby poles or fixtures (IV pole, anesthesia table, boom, etc.). In another aspect, rechargeable batteries are utilized to reduce waste and cost.

In another embodiment, a method is provided for using the laparoscopic filter system

BRIEF DESCRIPTION OF THE DRAWINGS

FIG. 3A is a system element diagram of the detachable filter cartridge in the first embodiment system shown in FIG. 1.

DETAILED DESCRIPTION OF THE EMBODIMENTS

Figure 1:
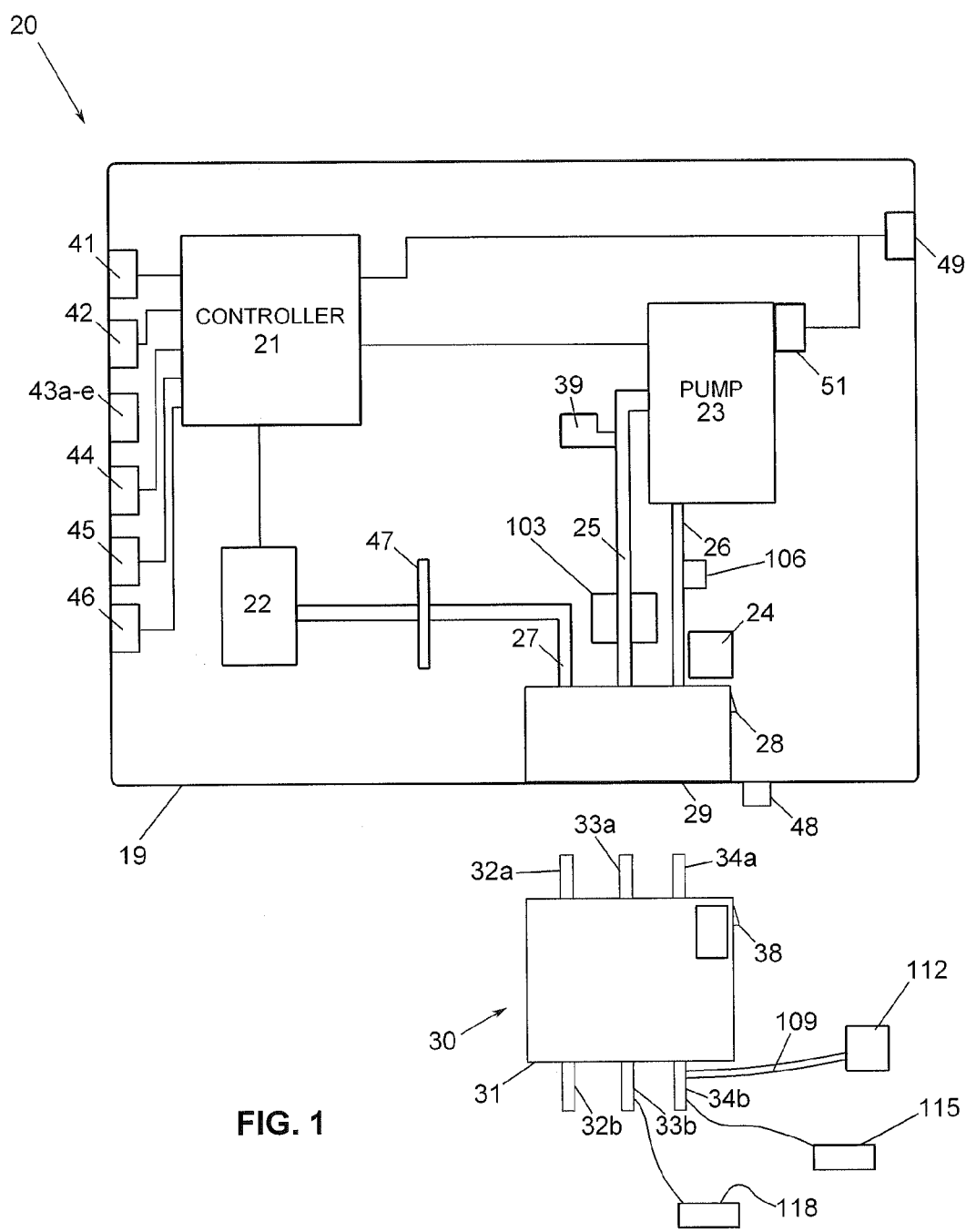
FIG. 1 is a system element diagram of a first embodiment filter system with the detachable filter cartridge detached from the main unit.

At the outset, it should be clearly understood that like reference numerals are intended to identify the same structural elements, portions or surfaces consistently throughout the several drawing figures, as such elements, portions or surfaces may be further described or explained by the entire written specification, of which this description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate. The following descriptions of embodiments are exemplary in nature and are not intended to restrict the scope of the present invention, the manner in which the various aspects of the invention may be implemented, or their applications or uses.

Referring now to the drawings, and more particularly to FIG. 1 thereof, provided is laparoscopic filter device, a first embodiment of which is generally indicated at 20. First embodiment system 20, is generally designed to evacuate smoke from an abdominal cavity during a laparoscopic procedure, while maintaining internal pressure and $CO_2$ or other gas volume.

Figure 2:
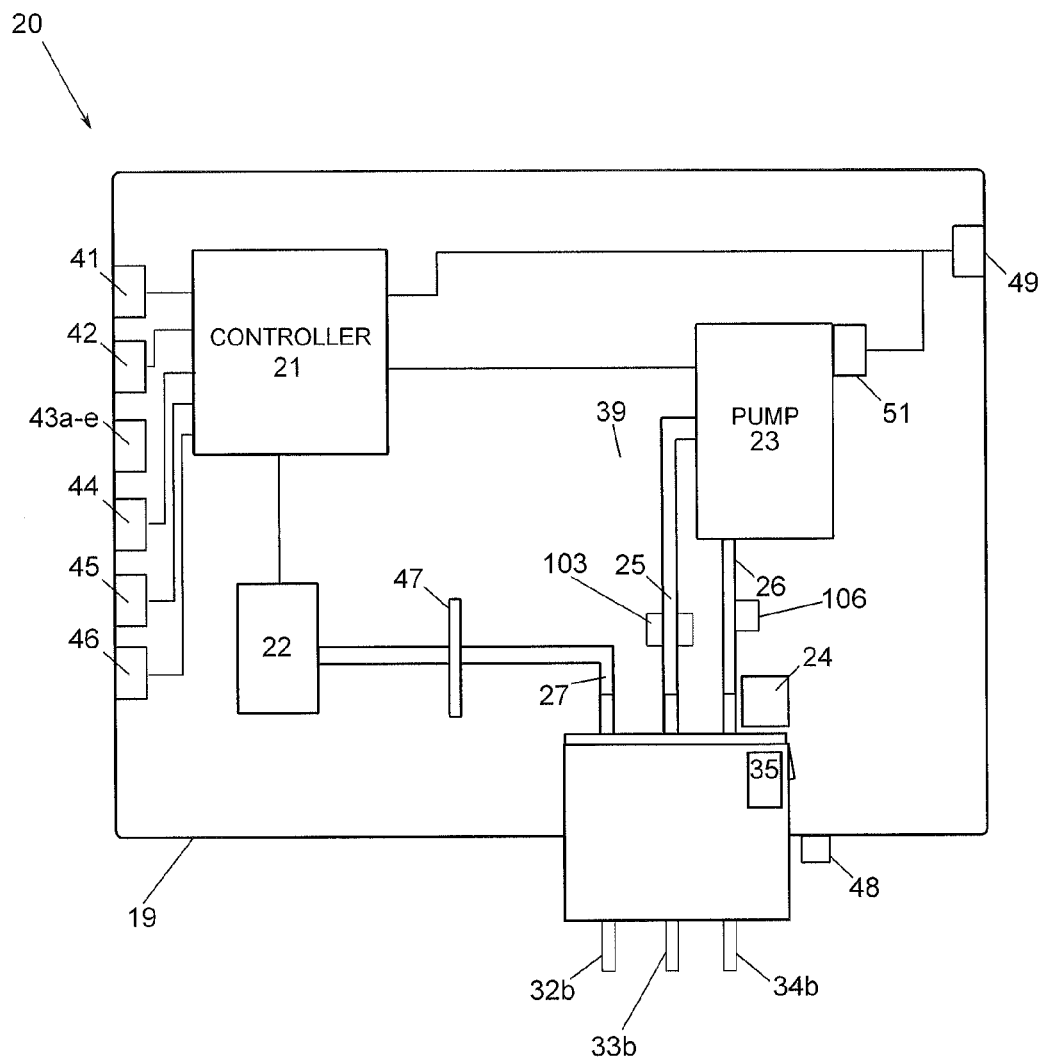
FIG. 2 is a system element diagram of the first embodiment filter system shown in FIG. 1 with the detachable filter cartridge attached to the main unit.
Figure 6:
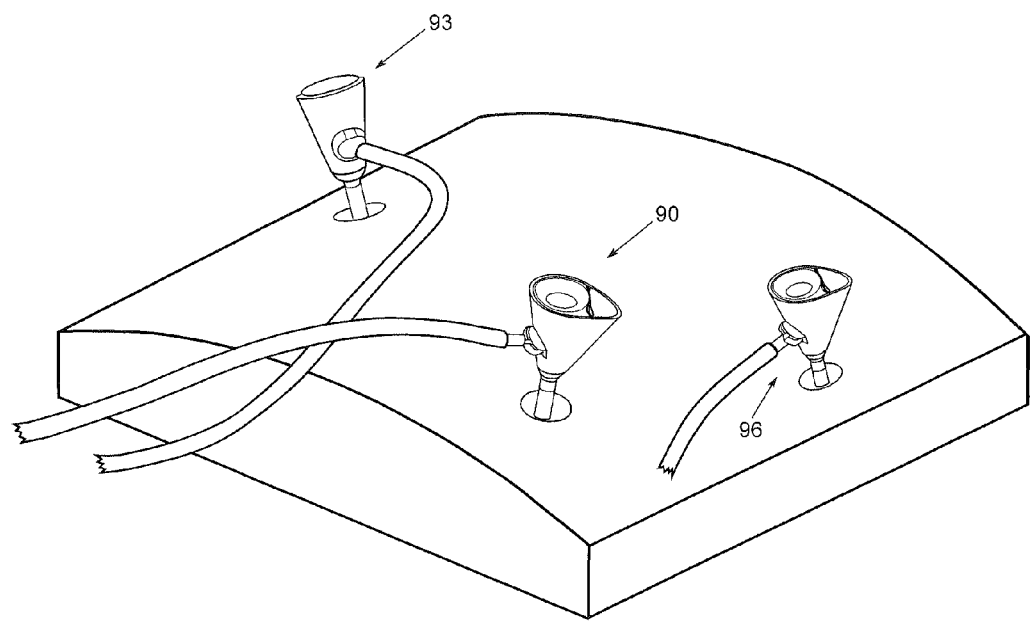
FIG. 6 is a perspective view of a laparoscopic system that connects to the first embodiment filter system.

As shown in FIG. 1, filter system 20 consists of main unit 19 and detachable filter cartridge 30. Main unit 20 has a plastic housing 19 with filter cartridge receiving chamber 29 which is configured and adapted to receive filter cartridge 30 as best shown in FIG. 2. Filter cartridge receiving chamber 29 has three ports: inflow line port 26, outflow line port 25, and pressure sensing line 27. A smoke sensor 106 may be positioned in the main unit upstream of the inlet to the pump 23. As an alternative, the filter cartridge 30 may be provided with a sampling port 109 for connecting a smoke sensor 112. Filter cartridge 30 contains three primary ports adapted to interface to the ports in receiving chamber 29. Filter cartridge 30 contains pressure sensing line unit side port 32a, outflow line unit side port 33a, and inflow line unit side port 34a, for interfacing with the respective receiving chamber 29 ports 27, 25, 26. Filter cartridge 30 also has three ports for interfacing with laparoscopic tubes which connect to three laparoscopic trocars 90, 93 and 96 as shown in FIG. 6. Filter cartridge 30 pressure sensing line patient side port 32b connects to trocar 90 used to sense the pressure within the laparoscopic surgery cavity. Filter cartridge 30 inflow line patient side port 34b connects to trocar 93 used to extract (or rather allow the escape of) gas from the surgical cavity. Also on filter cartridge 30 is outflow line patient side port 33b which connects to trocar 96 to return filtered gas back to the surgical cavity. Temperature sensors 115, 118 may be provided in the gas inflow and outflow lines to monitor the temperature of the gas being removed from the cavity and the temperature of the gas being returned to the cavity from the filter system 20.

As shown in FIGS. 1 and 2, main unit 20 and filter cartridge 30 are configured for reversible engagement. On housing 31 of filter cartridge 30 is lock or ridge 38 which locks into notch 28 in receiving chamber 29. Engagement between the filter cartridge 30 and the main unit 20 may be an engagement system that can be unlocked/released with a push of an external button or lever. For example, notch 28 holds lock 38 until release button 48 on unit 20 is pressed. Filter cartridge 30 contains RFID tag 35 which is arranged and configured to be read by RFID reader/writer 24 located on main unit 20. The RFID tag 35 may be used for authentication and/or for tracking the useful life of the filter cartridge 30.

Filter system 20 contains pump 23 which controls flow between pump inflow line 26 and pump outflow line 25. The filter system 20 may include a heater/humidifier 103 for warming and moisturizing the gas before it is returned to the cavity of the patient. Pump 23 may be a rolling piston pump. An example of a rolling piston pump assembly is model AP-60BF from Etonm Motor Co. Ltd. Pump 23 is controlled by controller 21. Current sensor 51 monitors the current drawn by pump 23. The filter system 20 may also contain a battery, a signal jack, a remote activation line, or a VGA output signal. The battery may be rechargeable, and the filter system may contain battery recharging circuitry. The filter system 20 may be configured to provide multi-language support. The filter system 20 may contain Bluetooth, Ethernet, wireless Ethernet, RS 232 transceivers or a general RF or audio detectors, and may provide status information or unit activation functionality through these elements. These communication links may interface with a central nursing station or with other devices within the operating room for data transfer.

The filter system 20 may further contain a speaker and the speaker may be used for providing alerts. Some alerts may be for detection of when the filter cartridge is expired, when the pressure is not within a desired range, when remaining battery life has dropped below a threshold, or when a laparoscopic line is disconnected or occluded.

The filter system 20 may further contain a power interface which provides the ability to be driven by an AC power supply, and may provide support for international AC power specifications. The power interface may also contain an emergency battery for allowing the unit to operate or safely shutdown after a power failure. The filter system may also contain a pressure relief valve to prevent pressure from exceeding a desired threshold. An ultraviolet lamp 39 may be included and configured to disinfect fluid passing through the filter system.

The filter system may also contain an attachment adapter for attaching the filter system to an IV pole, a bedside, a boom, a shelf, and/or a stand. The filter system may further contain acoustical insulation or vibration damping material.

Input power adapter 49 connects to external power, and provides power directly to controller 21 and pump 23. Additional power supply circuitry may be included to change the external power voltage characteristics.

Filter 47 is arranged to prevent any particles from passing from pressure sensing internal line 27 to pressure sensor 22. Pressure sensor 22 measures the pressure in the surgical site through the pressure sensing internal line 27, and provides the pressure reading to controller 21. Controller 21 is connected to several inputs and outputs including: on/off switch 41, pressure setting button 42, clear button 44, on/off LED 43a, a "pressure in range" LED (3b, digital or analog pressure reading LED 43c, filter maintenance LED 43d, error LED 43e, clear button 44, maintenance indicator 45, and auto activation line 46. The system is capable of detecting occlusion to disable the pump 23 to prevent injury. The on/off switch 41 may be controlled remotely via a wireless input to the controller 21 as will be evident to those of ordinary skill in the art based on this disclosure. Controller 21 is a microcontroller containing internal memory for program and variable storage as will be discussed. The system may include an LCD display screen used as a graphical user interface (GUI). The user interface may include a speed control to adjust flow. The flow may be adjusted based on many factors including patient size, physician preference, or the type of procedure being performed on the patient. The speed control may include various modes including a turbo mode where flow can be automatically increased rapidly over a short time period. A deflation mode may also be provided in which the return line 25 is diverted so that the system evacuates gas from the internal cavity. The interface may also provide a notification for under or over pressure conditions (initially preset by the user). Also, the internal pressure reading may be displayed to the operator.

FIG. 3A is a component layout view of filter cartridge 30. As shown in FIG. 3, filter cartridge contains second filter 39 in the outline unit flow path 33, and first filter 40 in the inflow line flow path 34. The first and second filters 39, 40 may be multilayer, hydrophobic, odor absorbing, or moisture absorbing. The first and second filters 39, 40 may contain ULPA elements or activated charcoal. The filters 39, 40 may comprise separate elements changed at different intervals. For example, a ULPA filter may be changed after a single patient, and a carbon filter may be changed after several patients. The filter cartridge 30 may be provided with a fluid dropout 100 located in the cartridge 30 upstream of the filter media 40. If fluid enters tube 34b, the fluid will drop in to the dropout 100 by gravity. A transparent window may be provided to observe the fluid level. The fluid dropout 100 or fluid trap may also be located outside and upstream of the filter cartridge 30.

Filter cartridge housing 31 may contain friction grips 50 (FIG. 8) in order to aid in pulling out and inserting filter cartridge 30 from/into filter system housing 19.

The cartridge 30 may also include a connection port 119 that may be connected to a conveying line 122 in fluid communication with an insufflator 125 for providing supplemental gas to the system as necessary. A control line 128 provides for actuation of the insufflator 125 by the controller 21. If the pressure inside the cavity indicates that supplemental gas is required then the insufflator 125 may be automatically activated by the controller 21 until the pressure inside the cavity reaches a suitable level.

Figure 3B:
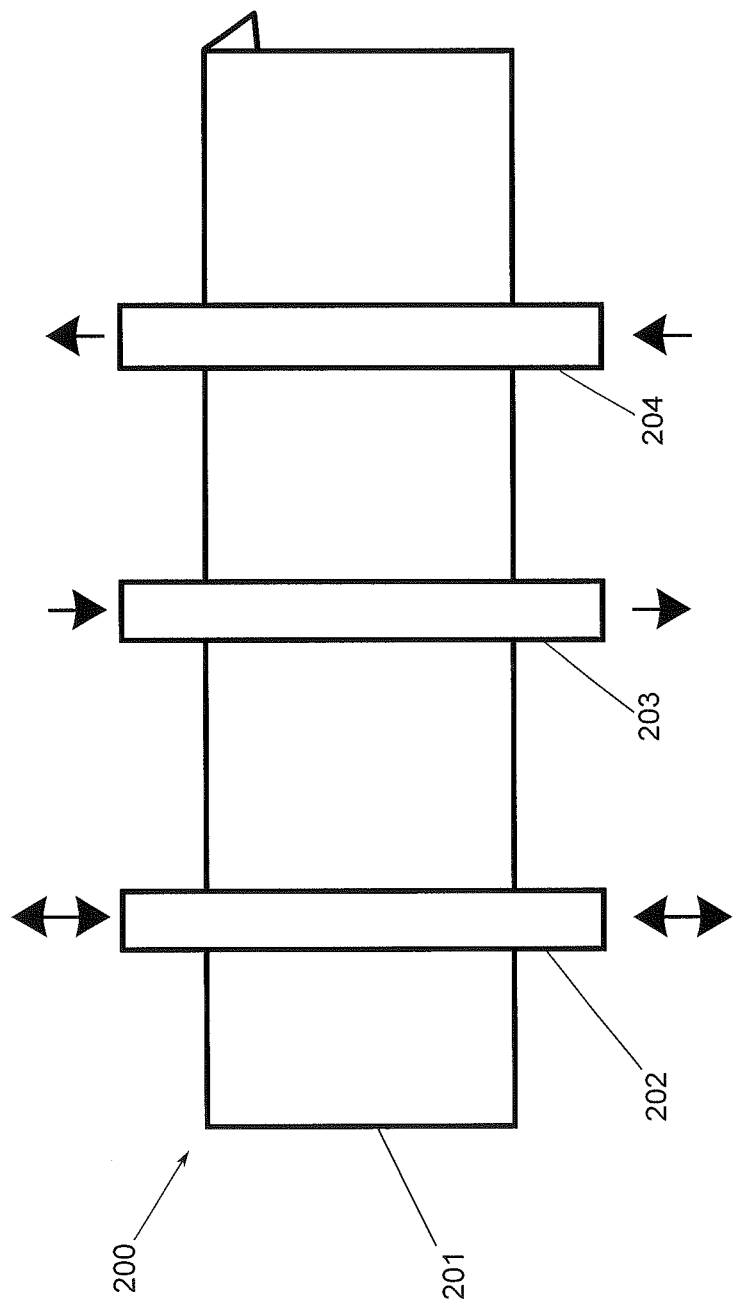
FIG. 3B is a system element diagram of a cleaning cartridge.

Turning to FIG. 3B, a cartridge 200 may be provided for introducing a cleaning solution into the main unit 20. A housing 201 contains parts 202, 203 and 204 for conveying the cleaning solution through lines 25, 26 and 27 in main unit 20.

Figure 4:
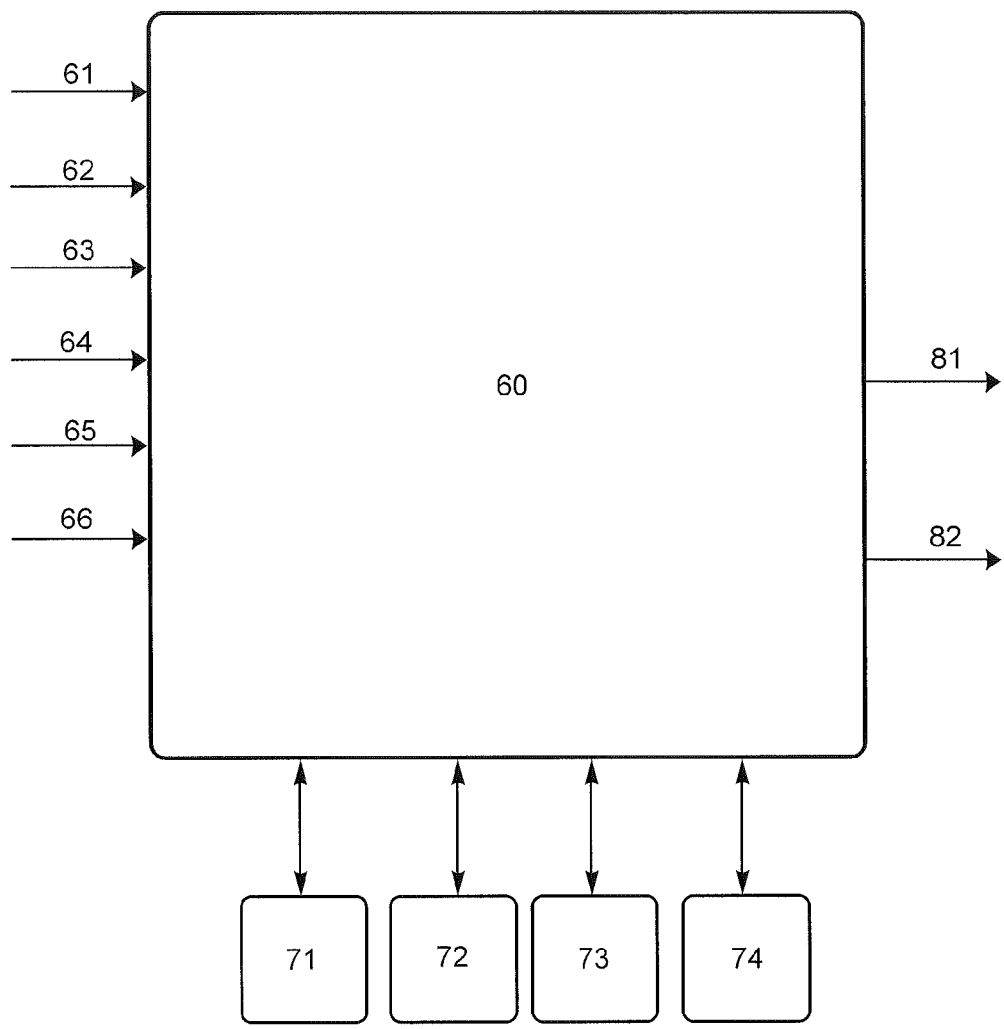
FIG. 4 is chart of the control algorithm in the first embodiment system shown in FIG. 1.

FIG. 4 is a chart of control algorithm 60 running on filter system 20. Control algorithm 60 receives several inputs including: on/off state signal 61, pressure signal 62, pressure setting button signals 63, clear button signal 64, current sensor signal 65, and other signals 66. Control algorithm 60 reads and writes several variable values during operation including: pressure setting 71, high pressure threshold 72, low pressure threshold 73, and filter lifetime state 74. Using each or some of the inputs and variable values, control algorithm produces output signals: pump on/off control 81 and LED signals 82. Also, using each or some of the inputs and variable values, control algorithm may write new values to the variables.

Figure 5:
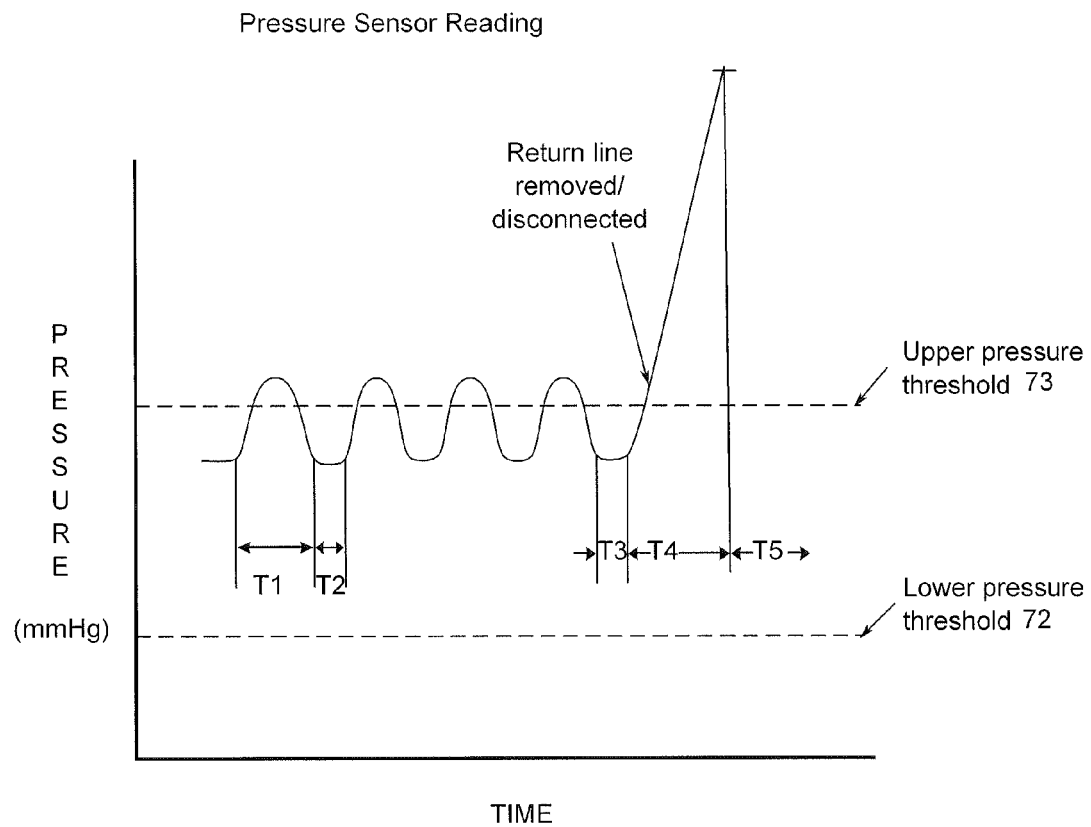
FIG. 5 is a graph of pressure sensor reading vs. time showing the automatic shut down capability of the first embodiment system shown in FIG. 1.

FIG. 5 is a graph of pressure sensor reading vs time showing the automatic shut down capability of the first embodiment system shown in FIG. 1. As shown in FIG. 5, the pressure during normal operation cyclically fluctuates at a pressure above lower pressure threshold 72 and periodically above upper pressure threshold 73. The control algorithm is configured to either read or ignore the pressure signal during specific time durations. A first time period T1 represents a time period during which the pressure signal is not measured and averaged for general processing. A second time period T2 represents a second time period T2 during which pressure is measured. Time period T3 represents a time period during which the pressure is measured right before the laparoscopic return line is disconnected. Time period T4 represents a duration in which the pressure signal is not measured and averaged, but during which the laparoscopic return line is disconnected. Time period T5 represents the time period after control algorithm 60 detects the disconnected laparoscopic return line and turns off the pump.

FIG. 6 represents the laparoscopic surgical setup in which three trocars 90, 93, and 96 are connected to the three lines from/to the filter. For example, trocar 90 is connected to pressure sensing line 32, trocar 93 is connected to outflow line 33, and trocar 96 is connected to inflow line 34.

Figure 7:
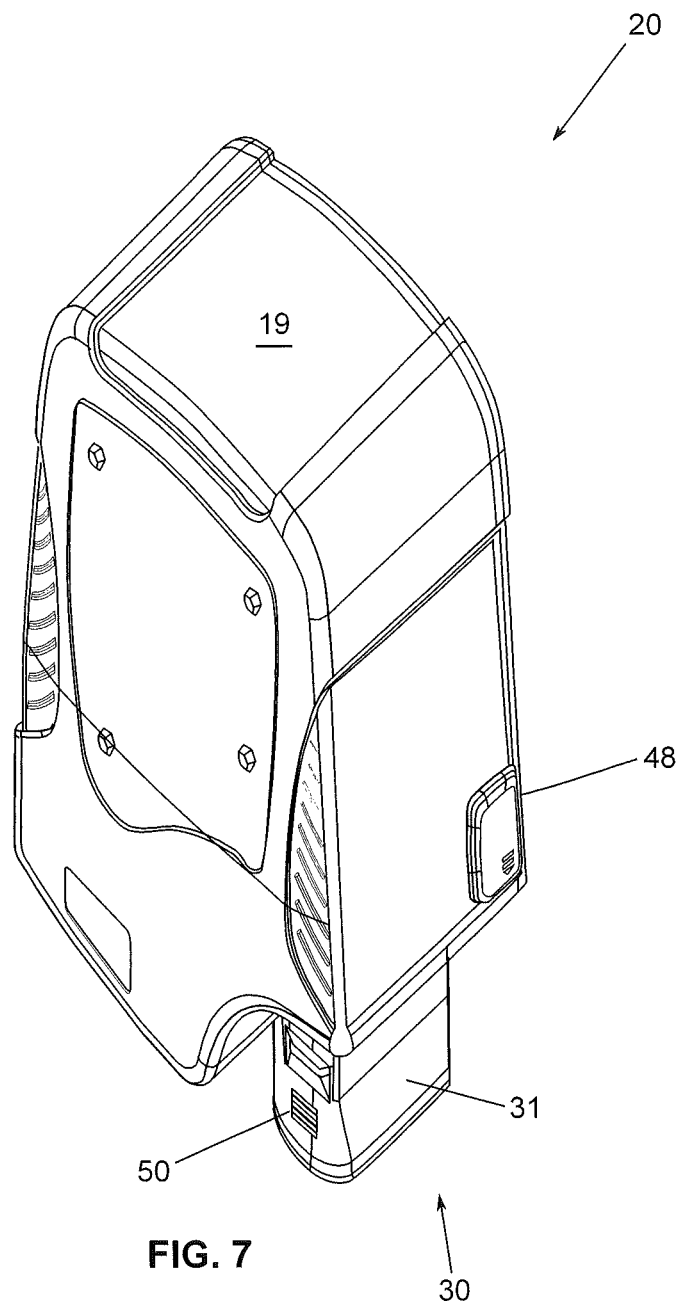
FIG. 7 is a perspective view of the filter cartridge of the first embodiment system.

In FIG. 7, one embodiment of filter housing 19 is shown. The filter housing 19 receives filter cartridge 30. Filter cartridge 30 may be provided with a housing 31 having friction grips 50 for manually inserting and removing the cartridge 30 from the housing 19. The filter housing 19 may be provided with a release button 48 for releasing a latch or other mechanism for holding the cartridge 30 in position.

Figure 8:
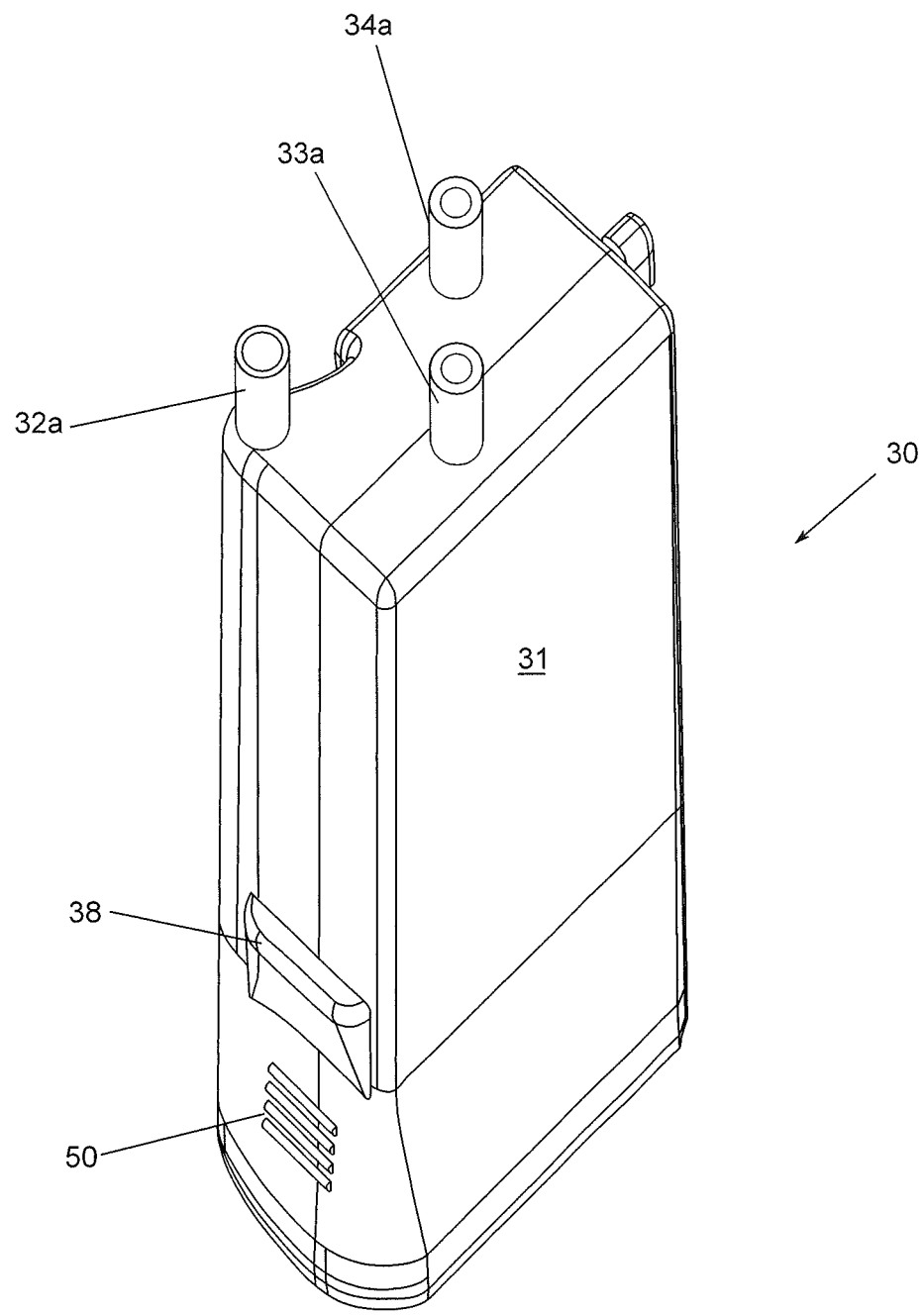
FIG. 8 is another perspective view of the filter cartridge of the first embodiment system.

Turning to FIG. 8, one embodiment of the filter cartridge 30 is shown in greater detail. The side of the cartridge 30 that engages with the filter system 20 (i.e., the "unit side" of the filter cartridge 30) is provided with an inflow line unit side port 34*a*, an outflow line unit side port 33*a*, and a pressure sensing line unit side port 32*a*. The filter cartridge 30 may be manually inserted by means of the friction grips 50. The body 31 may be provided with a lock or ridge 38 that is received in a corresponding latch in the main unit to hold the cartridge 30 in position.

Figure 9:
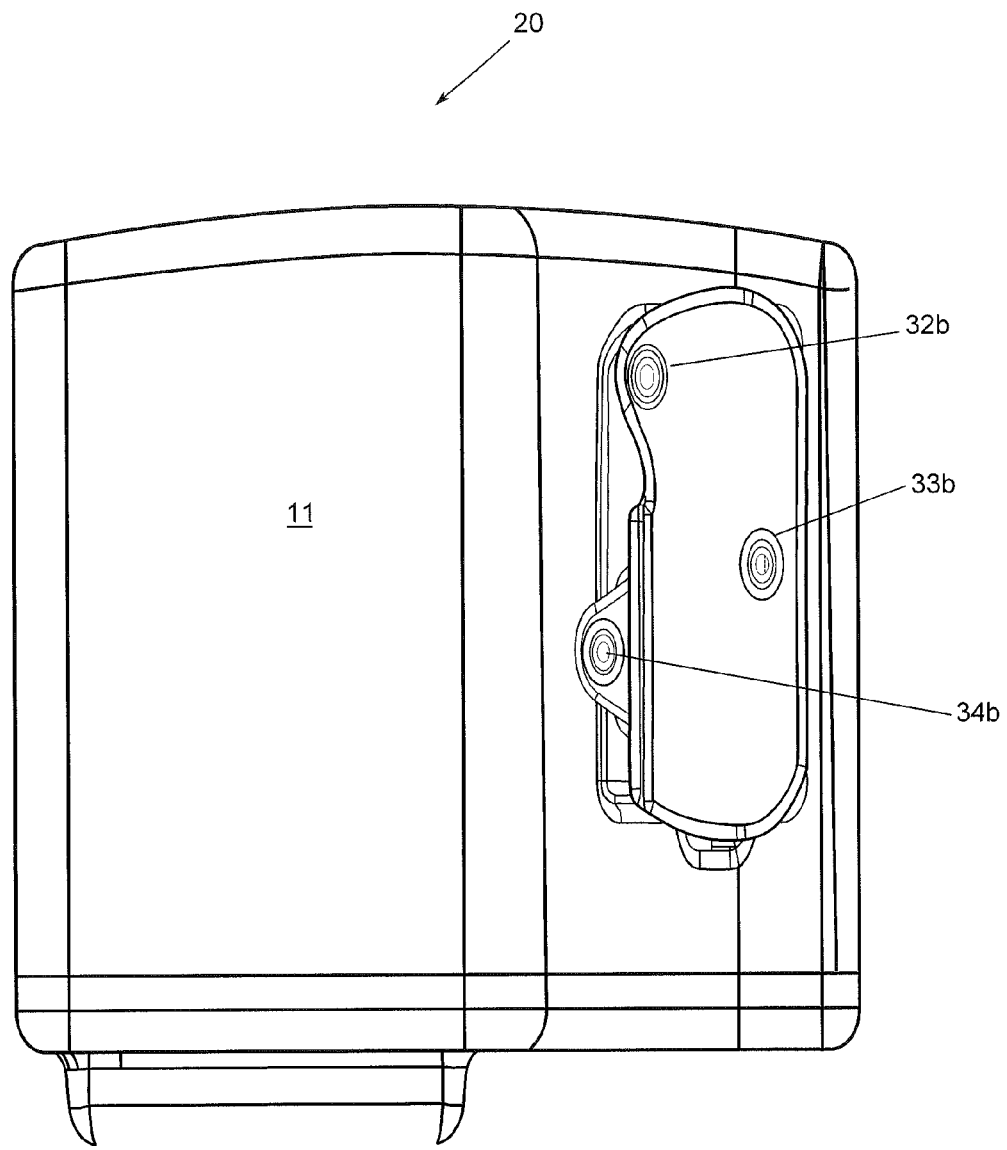
FIG. 9 is a bottom plan view of the filter cartridge in the first embodiment system.

Turning to FIG. 9, the side of the cartridge facing away from the main unit 20 (i.e., the "patient side" of the filter cartridge 30) is shown. The filter cartridge 30 contains three ports: pressure sensing line patient side port 32*b*; inflow line patient side port 34*b*; and outflow line patient side port 33*b*.

Figure 10:
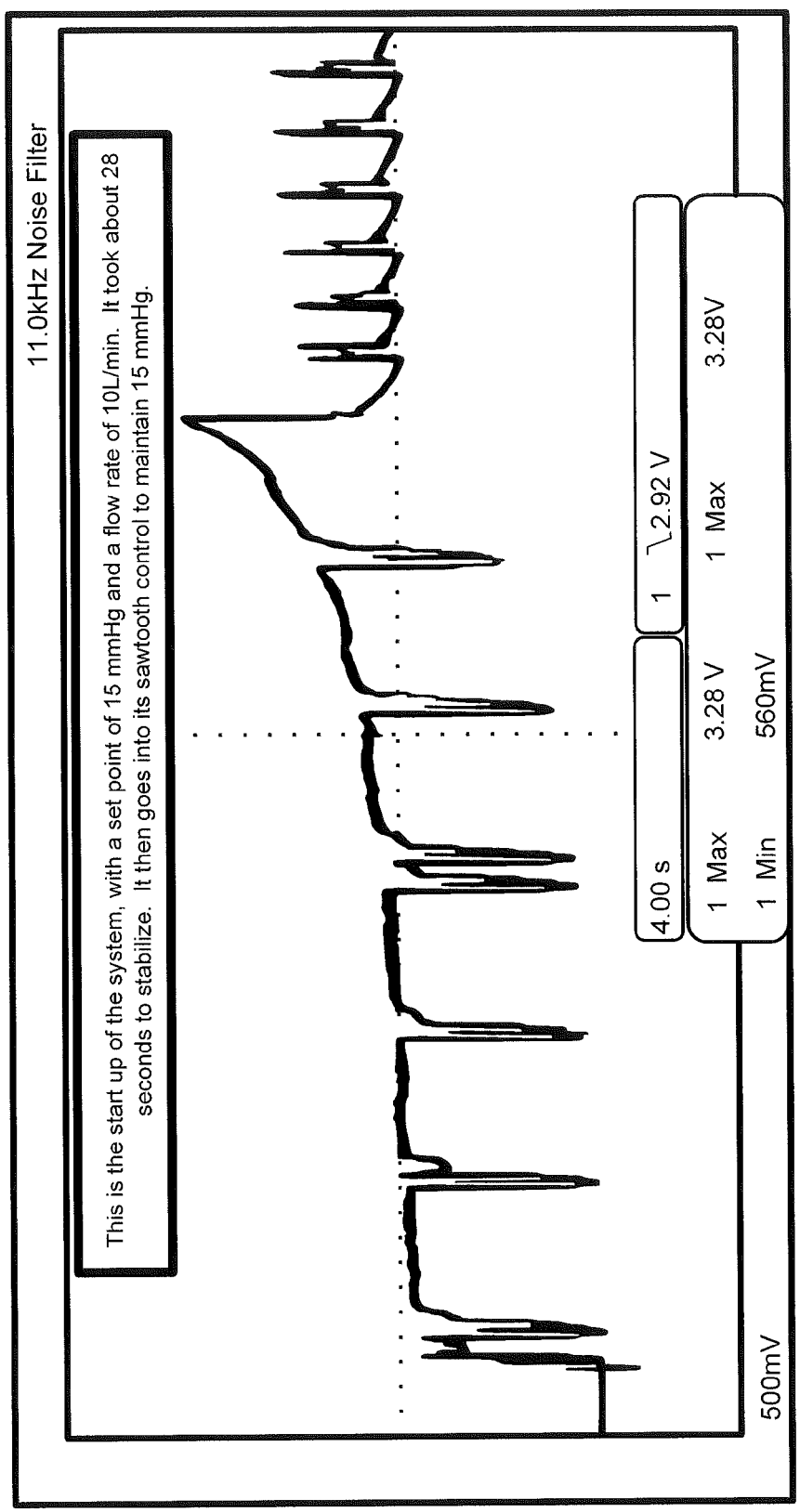
FIG. 10 is a pressure signal vs. time plot showing insufflator startup at 10 lpm.

Turning to FIG. 10, a graph of pressure versus time is shown during startup of the system. The example shown is for a set point of 15 mm Hg and a flow rate of 10 liters/minute. After approximately half a minute, the system stabilized and then went into a "saw tooth" control to maintain 15 mm Hg. Pressure is measured by the internal sensor through line 27.

Figure 11:
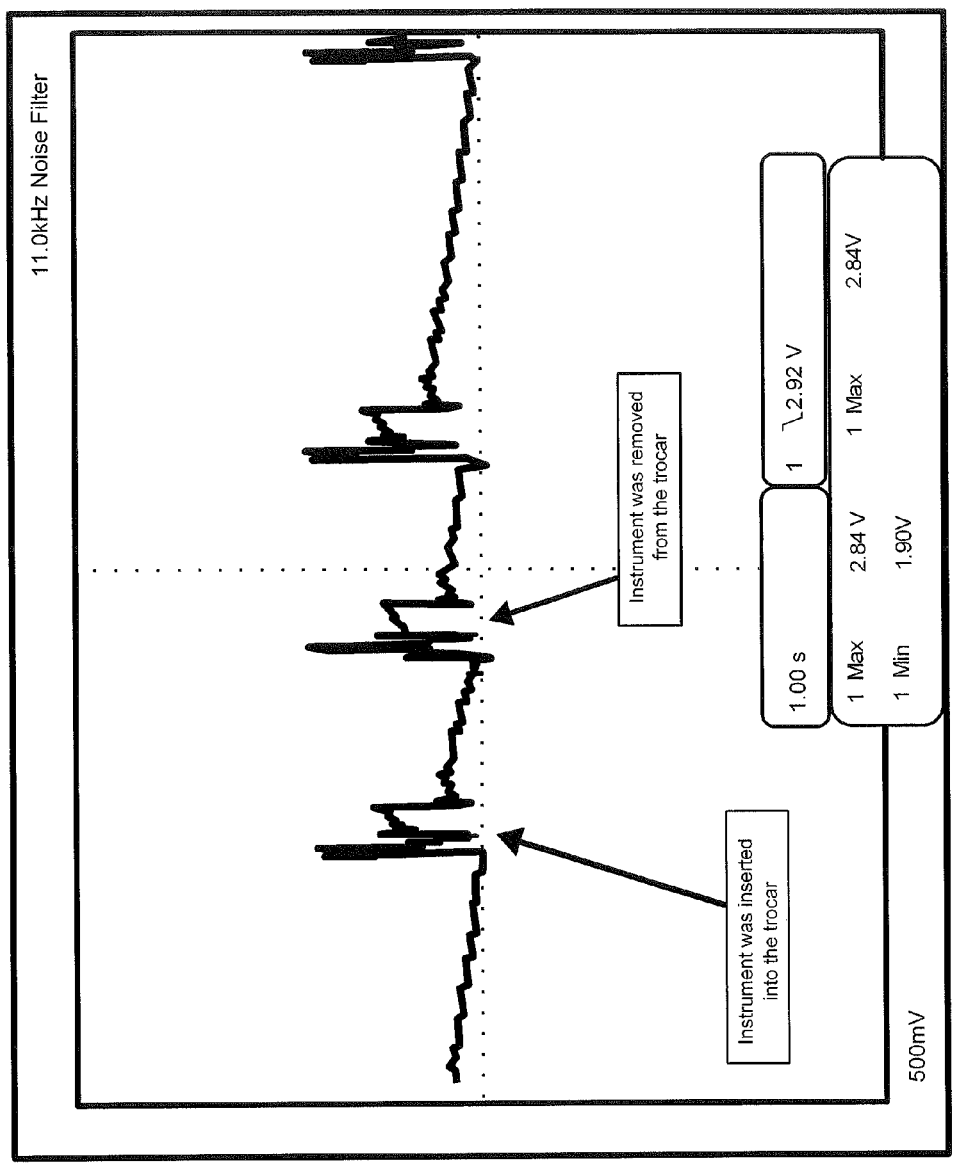
FIG. 11 is a pressure signal vs. time plot showing instrument insertion and removal events.

FIG. 11 is a graph of the pressure changes when an instrument is inserted and removed from the surgical site. The insertion of the instrument and the removal of the instrument results in spikes of internal pressure readings. The software recognizes this action and filters the data for continued operation when instruments are inserted and removed during the surgical case. Accordingly, this event is sensed by the system and is identified by the system without causing unnecessary stop and hold for pressure to restabilize.

Figure 12:
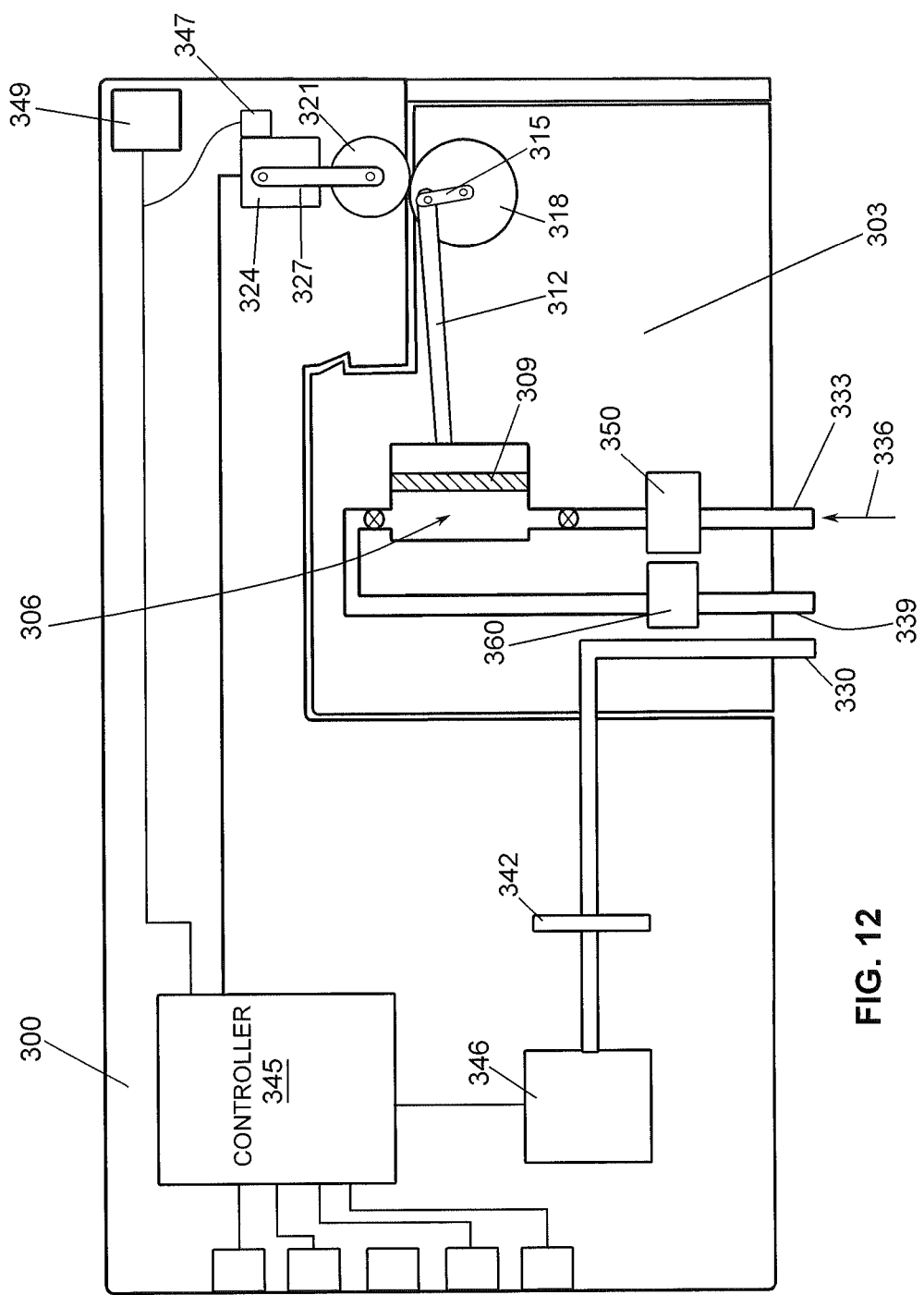
FIG. 12 is a system element diagram of a second embodiment of the filter system.
Figure 13:
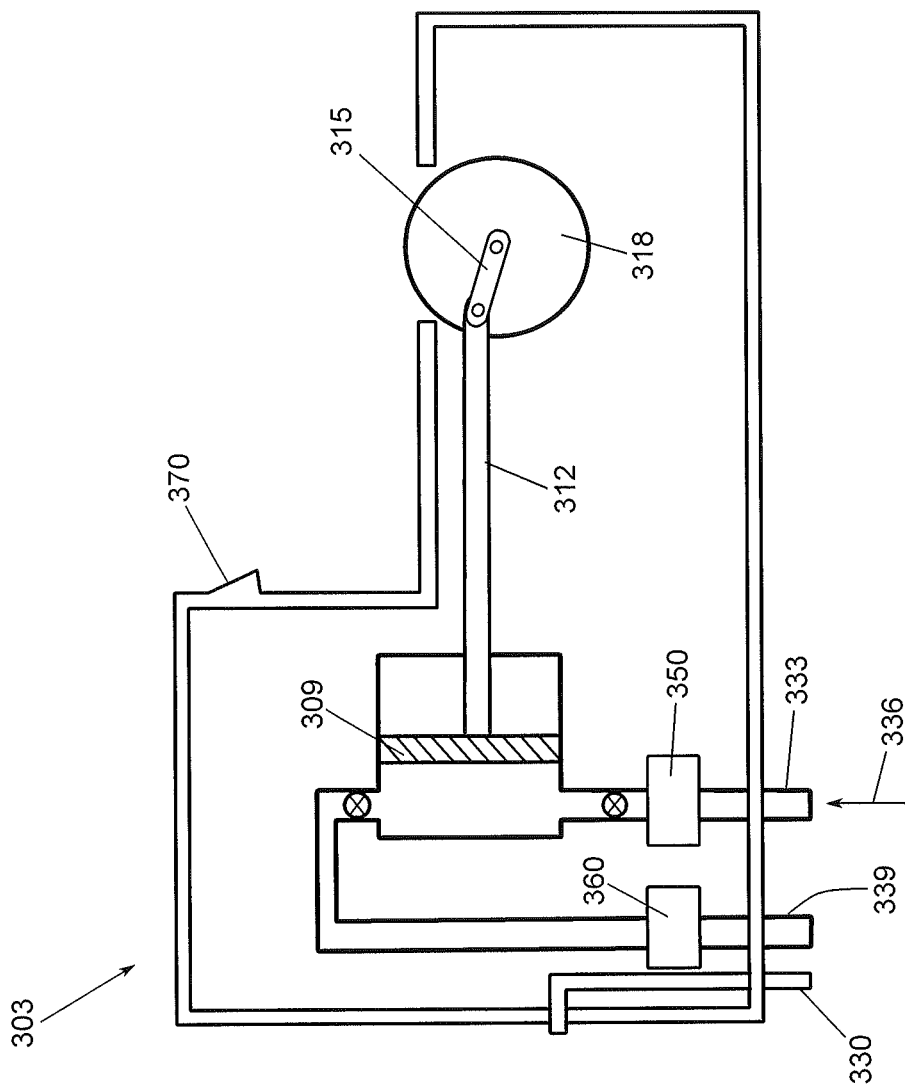
FIG. 13 is a system element diagram of the pump/filter assembly of FIG. 12.

Turning to FIG. 12, an alternate embodiment filter system includes a main unit 300 and a detachable pump/filter assembly 303 for single patient use. A diaphragm type pump may be provided with a pump chamber 306. The pump chamber 306 may be formed in the assembly 303 which is removable from the system 300. The chamber 306 may contain a diaphragm 309 moves in a reciprocating linear motion by operation of a rod 312 that may be connected to a crank 315 on a first mechanical element such as a rotating wheel 318. The wheel 318 may be driven by engagement (via gears or the like) with a second mechanical element such as a wheel 321 driven by a motor/gearbox 324 located in the main unit 300. The output of the motor/gearbox 324 may be transmitted to the wheel 321 by a belt 327, chain or the like. It will be evident to those of ordinary skill in the art based on this disclosure that the wheel is one example of a mechanical connection from the motor/gearbox 324 to the rod 312 for activating the pump/filter assembly 303. Other mechanical connections for driving the rod 312 of a diaphragm pump may also be suitable. The detachable pump/filter assembly 303 may include three ports. A first port may comprises a pressure sensing patient side port 330. A second port may comprise an inflow patient side port 333 for receiving gas from the cavity in the direction of arrow 336. A third port may comprise an outflow patient side port 339 for conveying filter gas back to the cavity. The pressure sensing line inside the main unit 300 may be provided with a filter 342. A controller 345 controls the flow rate of the pump and receives input from the sensors (i.e., pressure sensor 346 and current sensor 347). A power adapter 349 may be connected to an AC power supply. Filters 350 and 360 may be disposed in the lines in the pump/filter assembly 303. Turning to FIG. 13, the pump/filter assembly 303 is shown removed from the main unit 300 for clarity. The assembly 303 may be provided with a protuberance 370 for engaging with a recess 380 in the main unit 300. Engagement between the detachable pump/filter assembly 303 and the main unit 300 can be unlocked/released with a push of an external button or lever.

As an alternative, the pump/filter assembly 303 may include the motor/gearbox 324 such that the motor/gearbox 324 is also disposable.

Several surprising advantages resulted from the above described filter systems. For example, by using a dedicated trocar for pressure sensing that is separate from the inflow and outflow trocars, the pressure inside the surgical site could be more accurately monitored. The control algorithm allows the sensing of a disconnected trocar, which allows the filter to automatically shut down the filter motor such that the pressure in the surgical site does not exceed a critical value and the patient is not injured. Additionally, the use of a filter cartridge allows a user to easily change the filter media, without opening up a main unit, saving time and cost. Further, because the filter media has an RFID tag, its filter information and lifetime status can be effectively and easily monitored and tracked.

In a second embodiment, a filter system is designed and configured to be mounted on the side of a surgical bed or other nearby mounting fixture (IV pole, anesthesia table, etc.) via an attachment mounting mechanism. An example mounting mechanism mounts on a surgical bed rail and acts as an attachment mechanism that can be engaged or disengaged during a procedure. This gives medical staff the ability to relocate the smoke evacuation unit from the rail or IV pole to a patient's bed for convenience of use, for example. In addition, the amounting mechanism allows other tasks to be performed to the unit such as replacing the battery pack or turning unit on or off. In one aspect, an attachment/mounting mechanism accommodates various sizes of surgical bed rails, and some IV or anesthesia poles. A different style attachment/mounting mechanism connects to an IV or anesthesia pole for ease of placement of the unit around other equipment. One embodiment may also be placed on a surgical bed or other flat surface that does not require a special attachment mechanism.

The new apparatus and system is not limited to the foregoing embodiments. Those skilled in the art will recognize that other and further changes and modifications may be made thereto without departing from the spirit of the invention and design. Therefore, the apparatus, system and invention are not limited to the specific details and representative embodiments shown and described herein. In addition, the terminology and phraseology used herein is for purposes of description and should not be regarded as limiting.

The invention claimed is:

1. A filter system for use in connection with surgical smoke generated during medical procedures performed in a cavity, the system comprising:
    a main unit having an inflow port, an outflow port and a pressure sensing port, the main unit having a receiving chamber disposed thereon;
    a pump contained within the main unit for conveying the surgical smoke through the filter system;
    a controller contained within the main unit configured to operate the pump to control the flow of the surgical smoke through the system, the controller having a user interface;
    a filter cartridge configured to removably attach to the receiving chamber on the main unit, the filter cartridge having an inflow pass-through line configured to interface with the inflow port, an outflow pass-through line configured to interface with the outflow port, and a pressure sensing pass-through line configured to interface with the pressure sensing port; and,
    a filter media arranged in series with said inflow passthrough line.

2. The filter system of claim 1, wherein a pressure sensor is disposed in fluid communication, via the pressure sensing port, with a cannula disposed in the cavity.

3. The filter system of claim 1, further comprising an insufflator disposed in fluid communication with the outflow port, the insufflator capable of providing supplemental gas to the system in order to maintain a desired pressure inside the cavity.

4. The filter system of claim 1, further comprising a heater arranged in series with the outflow port, the heat arranged and configured to warm and to humidify the gas being returned to the cavity.

5. The filter system of claim 1, wherein the controller automatically detects when a cannula connected to the filter system at one of the ports is occluded.

6. The filter system of claim 1, further comprising a fluid dropout disposed in fluid communication with the inflow port.

7. The filter system of claim 1, wherein the controller automatically detects when a cannula connected to the filter system is disconnected from a port selected from the group consisting of the inflow port, outflow port and pressure sensing port.

8. A filter system for use in connection with surgical smoke generated during medical procedures performed in a cavity, the system comprising:
    a main unit having an inflow port, an outflow port, a pressure sensing port and a receiving chamber disposed thereon;
    a controller contained within the main unit configured to control the flow of the surgical smoke through the system, the controller having a user interface;
    a pump/filter assembly having a pump chamber, the pump/filter assembly configured to removably attach to the receiving chamber on the main unit, the pump/filter assembly having an inflow pass-through line, an outflow passthrough line, and a pressure sensing passthrough line; and,
    a filter media arranged in series with said inflow passthrough line, wherein a pressure sensor is disposed in fluid communication, via the pressure sensing port, with a cannula disposed in the cavity.

9. The filter system of claim 8, wherein the pump/filter assembly further comprises a diaphragm disposed in the pump chamber, the diaphragm connected to a rod.

10. The filter system of claim 9, wherein the rod is connected to a crank rotated on a first mechanical element disposed on the pump/filter assembly.

11. The filter system of claim 10, wherein the first mechanical element engages with a second mechanical element disposed in the main unit, the second mechanical element operatively connected to a motor/gearbox disposed in the main unit, the second mechanical element providing a driving force to the first mechanical element to operate the diaphragm in the pump chamber when the pump/filter assembly is attached to the main unit.

12. The filter system of claim 8, further comprising an insufflator disposed in fluid communication with the outflow port, the insufflator capable of providing supplemental gas to the system in order to maintain a desired pressure inside the cavity.

13. The filter system of claim 8, further comprising a heater arranged in series with the outflow port, the heat arranged and configured to warm and to humidify the gas being returned to the cavity.

14. The filter system of claim 8, wherein the controller automatically detects when a cannula connected to the filter system at one of the ports is occluded.

15. The filter system of claim 8, further comprising a fluid dropout disposed in fluid communication with the inflow port.

16. The filter system of claim 8, wherein the controller automatically detects when a cannula connected to the filter system is disconnected from a port selected from the group consisting of the inflow port, outflow port and pressure sensing port.

17. The filter system of claim 8, wherein the pump/filter assembly further comprises a motor.

18. A method for filtering surgical smoke generated during medical procedures performed in a cavity, the method comprising:
    providing a main unit having an inflow port, an outflow port and a pressure sensing port, the main unit having a receiving chamber disposed thereon;
    providing a pump contained within the main unit for conveying the surgical smoke through the filter system;
    providing a controller contained within the main unit configured to operate the pump to control the flow of the surgical smoke through the system, the controller having a user interface;

providing a filter cartridge configured to removably attach to the receiving chamber on the main unit, the filter cartridge having an inflow pass-through line configured to interface with the inflow port, an outflow passthrough line configured to interface with the outflow port, and a pressure sensing pass-through line configured to interface with the pressure sensing port;

providing a filter media arranged in series with said inflow pass-through line;

providing a first conduit between the cavity and the pressure sensing pass-through line;

providing a second conduit between the cavity and the inflow pass-through line;

providing a third conduit between the cavity and the outflow pass-through line;

providing a pressure sensor disposed in fluid communication with the cavity and the pressure sensing passthrough line;

providing an insufflator in fluid communication with an outflow pass through port;

wherein the controller receives input from the pressure sensor regarding the pressure inside the cavity and automatically adjusts the flow of surgical smoke through the system based on detected pressure inside the cavity.

19. The method of claim 18 wherein the controller diverts the flow from the outflow pass-through line in order to deflate the cavity.

20. The method of claim 18, further comprising providing a cleaning cartridge for introducing a cleaning solution into the main unit.

\* \* \* \* \*